(12) United States Patent
Verma et al.

(10) Patent No.: US 7,819,825 B2
(45) Date of Patent: Oct. 26, 2010

(54) REMOTE CERVICAL DILATION MONITORING SYSTEM AND METHOD

(75) Inventors: Pramode Verma, Tulsa, OK (US); Anjan Ghosh, Tulsa, OK (US); James J. Sluss, Jr., Broken Arrow, OK (US); Samuel Cheng, Tulsa, OK (US); Mark G. Martens, Jenks, OK (US); Robert Huck, Tulsa, OK (US); Shanshan Chen, Tulsa, OK (US); Anil K. Kaul, Tulsa, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 192 days.

(21) Appl. No.: 12/053,321

(22) Filed: Mar. 21, 2008

(65) Prior Publication Data

US 2009/0240168 A1   Sep. 24, 2009

(51) Int. Cl.
*A61B 5/103* (2006.01)
*A61B 5/117* (2006.01)

(52) U.S. Cl. .................. 600/588; 600/591; 128/903

(58) Field of Classification Search ............... 600/300, 600/304, 587, 588, 591; 128/903
See application file for complete search history.

(56) References Cited

U.S. PATENT DOCUMENTS

| | | | |
|---|---|---|---|
| 3,768,459 A | 10/1973 | Cannon et al. | |
| 4,141,345 A | 2/1979 | Allen et al. | |
| 4,147,160 A * | 4/1979 | Aranow et al. | 600/588 |
| 4,682,609 A | 7/1987 | Parsons | |
| 4,719,925 A | 1/1988 | Parsons | |
| 5,450,857 A | 9/1995 | Garfield et al. | |
| 5,876,357 A | 3/1999 | Tomer | |
| 6,039,701 A | 3/2000 | Sliwa et al. | |
| 6,066,104 A | 5/2000 | Dao et al. | |
| 6,270,458 B1 | 8/2001 | Barnea | |
| 6,419,646 B1 | 7/2002 | Baxter-Jones | |
| 6,423,000 B1 * | 7/2002 | Berry | 600/304 |
| 6,450,977 B1 | 9/2002 | Baxter-Jones | |
| 6,524,259 B2 | 2/2003 | Baxter-Jones et al. | |
| 6,802,817 B2 | 10/2004 | Baxter-Jones et al. | |
| 6,966,881 B2 | 11/2005 | Ben-Cnaan et al. | |
| 6,994,678 B2 | 2/2006 | Baxter-Jones et al. | |
| 2002/0028995 A1 * | 3/2002 | Mault | 600/437 |
| 2002/0035878 A1 * | 3/2002 | Norton | 73/862.391 |
| 2005/0277841 A1 * | 12/2005 | Shennib | 600/511 |

* cited by examiner

*Primary Examiner*—Max Hindenburg
*Assistant Examiner*—Jonathan M Foreman
(74) *Attorney, Agent, or Firm*—Dunlap Codding, P.C.

(57) ABSTRACT

A cervical dilation monitor for measuring the dilation of a cervix and for providing cervical data to an external wireless unit. The cervical dilation monitor comprises a housing, a sensor, a controller, and a power source. The housing is constructed of a biocompatible material and is adapted to be connected to portions of a cervical lip. The sensor is supported by the housing so as to generate signals related to cervical dilation. The controller includes a transceiver and a processor. The transceiver receives and transmits the cervical dilation data to the external wireless unit. The processor receives the signals generated by the sensor related to the cervical dilation and enables the transceiver to wirelessly transmit the cervical dilation data. The power source provides power to the controller.

7 Claims, 7 Drawing Sheets

```
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
The length is now 5cm
```

*Fig. 10b*

REMOTE CERVICAL DILATION MONITORING SYSTEM AND METHOD

CROSS-REFERENCE TO RELATED APPLICATIONS

Not applicable.

STATEMENT REGARDING FEDERALLY SPONSORED RESEARCH AND DEVELOPMENT

Not applicable.

BRIEF DESCRIPTION OF THE SEVERAL VIEWS OF THE DRAWING

So that the above recited features and advantages of the present invention can be understood in detail, a more particular description of the invention, briefly summarized above, may be made by reference to the embodiments thereof that are illustrated in the appended drawings. It is to be noted, however, that the appended drawings illustrate only typical embodiments of this invention and are therefore not to be considered limiting of its scope, for the invention may admit to other equally effective embodiments.

FIG. 10B is a graphical view depicting a terminal display on a remote monitoring terminal constructed in accordance with the present invention.

DETAILED DESCRIPTION OF THE INVENTION

Figure 1:
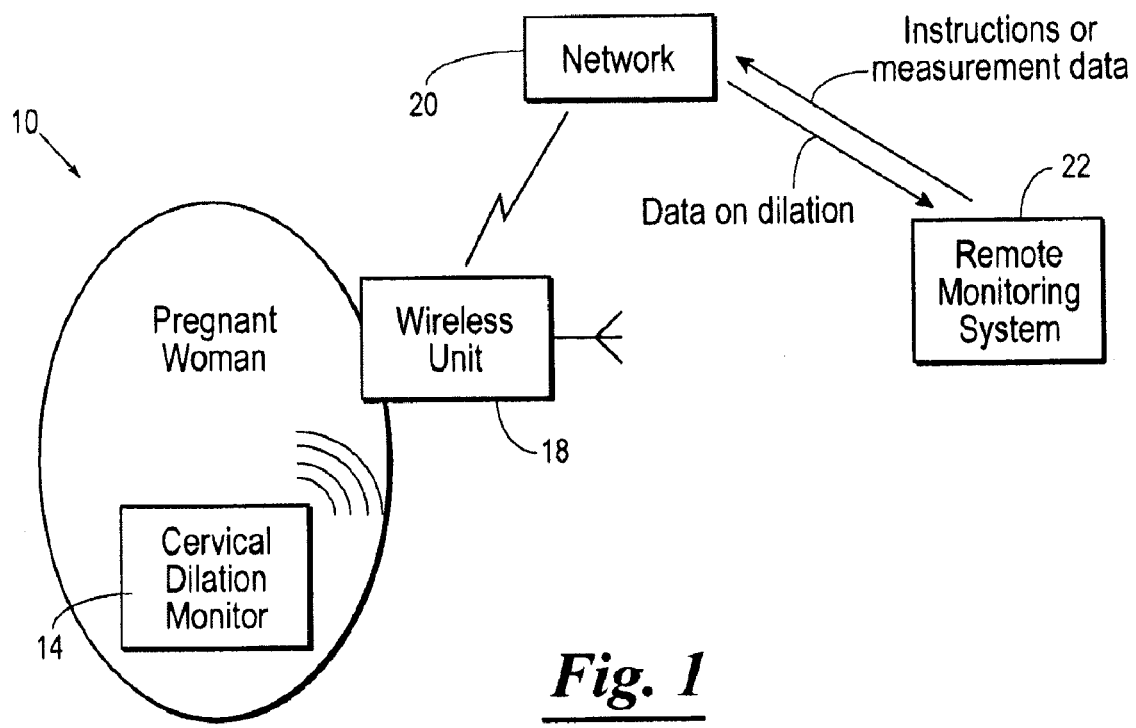
FIG. 1 is a schematic diagram of one version of a remote cervical dilation monitoring system constructed in accordance with the present invention.

Presently preferred embodiments of the invention are shown in the above-identified figures and described in detail below. In describing the preferred embodiments, like or identical reference numerals are used to identify common or similar elements. The figures are not necessarily to scale and certain features and certain views of the figures may be shown exaggerated in scale or in schematic in the interest of clarity and conciseness.

Referring now to the drawings, and in particular to FIG. 1, shown therein and designated by a reference numeral 10 is a preferred embodiment of a remote cervical dilation monitoring system constructed in accordance with the present invention. In general, the system 10 is provided with a cervical dilation monitor 14, a wireless unit 18, a network 20 and a remote monitoring system 22. The cervical dilation monitor 14 measures changes in cervical diameter. The cervical dilation monitor 14 (best seen in FIGS. 2 and 3a-3d) senses cervical dilation data and wirelessly transmits this data, or other data indicative of the dilation of the cervix, to the wireless unit 18. While FIG. 1 shows the system 10 in relation to a pregnant woman, it should be understood the system 10 can be used for monitoring cervical dilation of a human or a non-human, pregnant female animal. For instance the system 10 could be used to monitor the cervical dilation of a pregnant female horse, and the wireless unit 18 could be used by a farmer/rancher or a veterinarian to ascertain the immediacy of labor of the animal. The wireless unit 18 receives the cervical dilation data and then transmits the cervical dilation data to the network 20 which then transmits this data to the remote monitoring system 22 which continuously, and in real time, monitors the level and magnitude of cervical dilation. The remote monitoring system 22 then transmits instructions or data back to the network 20 which then transmits these instructions or data back to the wireless unit 18 (or the pregnant female's physician or doctor's office) which notifies the woman of the level of cervical dilation and the immediacy of labor based on the level of cervical dilation or the rate of change of the cervical dilation.

Figure 2:
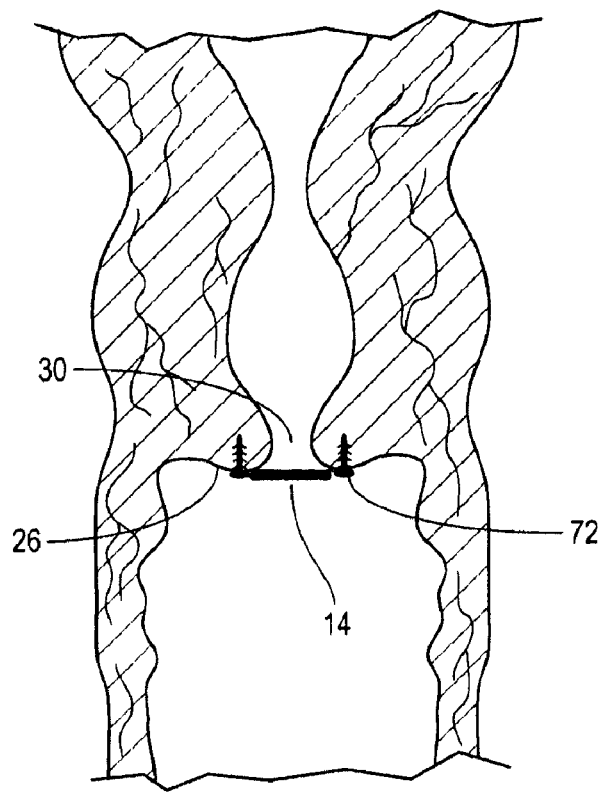
FIG. 2 is a cross-sectional view of a vaginal cavity illustrating a cervical dilation monitor constructed in accordance with the present invention installed on at least two portions of a cervical lip for measuring dilation of the cervix.
Figure 3A:
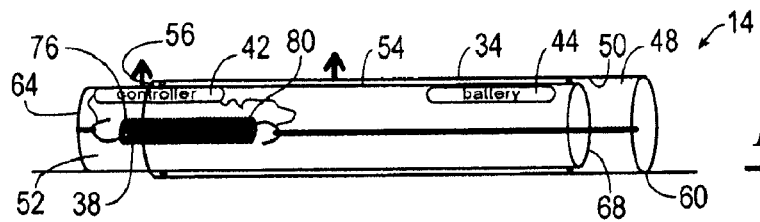
FIGS. 3A-3D are detailed, perspective views showing the cervical dilation monitor at different dilations of the cervix.
Figure 3B:
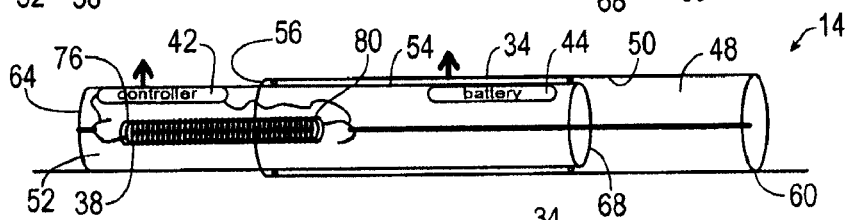
Figure 3C:
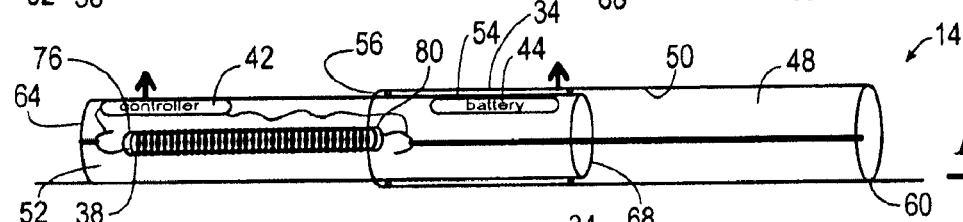
Figure 3D:
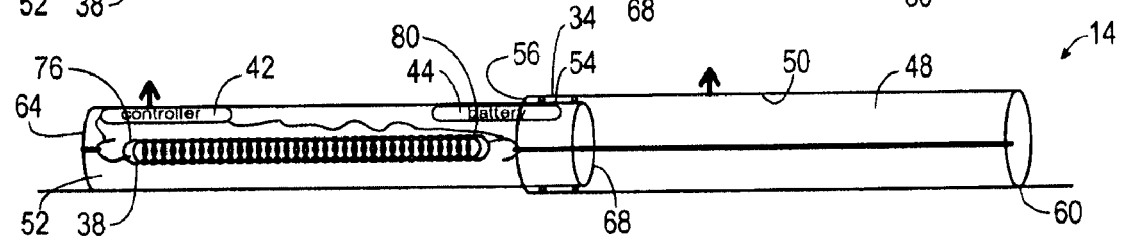

Referring now to FIGS. 2 and 3A-3D, shown in FIG. 2 is a drawing of the cervical dilation monitor 14 attached to portions of a cervical lip 26. While FIG. 2 shows the cervical dilation monitor 14 extending across a cervical opening 30, it should be understood that the cervical dilation monitor 14 need not be in this orientation to accomplish the objectives of the present invention. For instance, the cervical dilation monitor 14 can be oriented so that the cervical dilation monitor 14 generally extends about the cervical opening 30. As shown in FIGS. 3A-3d, in general, the cervical dilation monitor 14 includes: a housing 34; a sensor 38, supported by the housing 34, which generates signals associated with cervical dilation; a controller 42 which receives the signals generated by the sensor 38 and transmits these signals to the remote monitoring system 22; and a power source 44 which provides power to the controller 42.

The housing 34 preferably includes a hollow outer portion 48 and a hollow inner portion 52. The outer portion 48 has an unsealed first end 56 and a sealed second end 60. Similarly, the inner portion 52 has a sealed first end 64 and an unsealed second end 68. The inner portion 52 is disposed within the outer portion 48 such that space exists between an inner peripheral surface 50 of the outer portion 48 and the outer peripheral surface 54 of the inner portion 52. The inner and outer portions 48 and 52 are illustrated as a cylinder. While FIGS. 3A-3D illustrate the housing 34 to be a circular-shaped cylinder, it should be understood that the housing 34 can be of any shape or configuration that accomplishes the objectives of the present invention.

Figure 7:
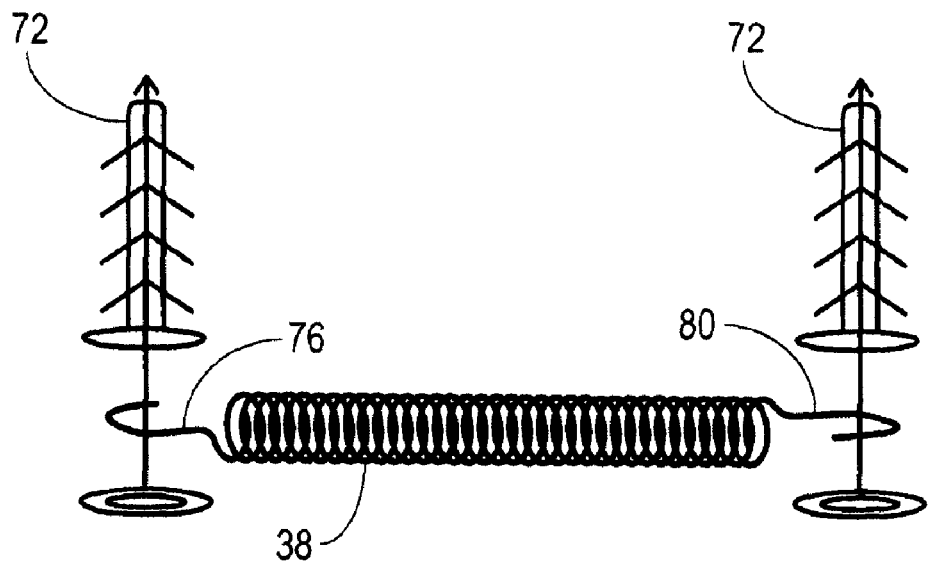
FIG. 7 is a perspective view of a coil of the cervical dilation monitor and two connectors used to connect the cervical dilation monitor to the portions of the cervical lip.

The sealed second end 60 of the outer portion 48 is connected to a connector 72 (shown best in FIG. 7), which anchors the housing 34 of the cervical dilation monitor 14 to a portion of the cervical lip 26. Similarly, the sealed first end 64 of the inner portion 52 is connected to a connector 72, which also anchors the housing 34 of the cervical dilation monitor 14 to portions of the cervical lip 26. Thus, when the second end 60 of the outer portion 48 and the first end 64 of the inner portion 52 are connected to their respective anchored connectors 72, the housing 34 of the cervical dilation monitor 14 is situated in a manner so as to slidably extend in accordance with the level of cervical dilation of the pregnant female. Other attachment locations of the cervical dilation monitor 14 can be at any points along the circumference of the outer body of the cervical opening 30. While FIG. 2 depicts the housing 34 anchored through the bottom portions of the cervical lip 26, the housing need not be in this orientation, and can be, for instance, anchored to any portions of the cervical lip 26. In addition, while the figures depict the housing 34 connected to the connectors 72 by a hook and loop mechanism, it should be understood that the connectors 72 can be any structure suitable to secure the housing 34 to the connectors 72. The housing 34 and the connectors 72 may also be unitary in structure. The connectors 72, although shown as barbed in FIG. 7, can be of any configuration (for example, backed-posts, clips, or stitches) suitable for anchoring or securing the connectors 72 to portions of the cervical lip 26. The connectors 72 are preferably constructed of a biocompatible material or coated with a biocompatible material, including, but not limited to, stainless steel, Teflon®, silicone rubber, hydrophilic coatings, titanium, plastic, or polymer materials.

In a preferred embodiment, the housing 34 is constructed in a manner which allows the outer portion 48 and inner portion 52 to telescopically move in relation to one another. Thus, when the housing 34 is connected to the connectors 72 anchored to portions of the cervical lip 26, the act of cervical dilation causes the outer portion 48 and the inner portion 52 to slidably telescope apart relative to each other. The housing 34, and all of its constituent parts, are preferably constructed of a biocompatible material or coated with a biocompatible material, including, but not limited to, stainless steel, Teflon, silicone rubber, hydrophilic coatings, titanium, non-reactive plastic, or polymer materials. Additionally, while the housing 34 is primarily depicted as being rigid in structure, it should be understood that the housing 34 can be formed of a non-rigid, flexible material. The sensor 38 is supported by the housing 34 and generates signals related to cervical dilation. In a preferred embodiment, the sensor 38 generally includes a first end 76 and a second end 80.

The sensor 38 is preferably disposed within the inner portion 52 of the cervical dilation monitor 14. In a preferred embodiment, the first end 76 of the sensor 38 is connected to the sealed first end 64 of the inner portion 52, while the second end 80 of the sensor 38 is connected to the sealed second end 60 of the outer portion 48. As the outer portion 48 and inner portion 52 slidably telescope apart in response to an increase in cervical dilation, the sensor 38 is likewise stretched apart. The preferred embodiment of the sensor 38 is a coil that changes inductance as the coil is stretched, but the sensor 38 can be any configuration or device(s) that would allow for accurate measurement associated with changes in position of the outer and inner portions 48 and 52 of the housing 34. In addition, while the preferred embodiment describes an electrical sensor that measures changes in inductance, it should be understood that the sensor 38 need not be limited to an electrical sensor and may include, but not by way of limitation, an ultrasonic sensor, an optical sensor, or a temperature sensor.

The cervical dilation monitor 14 also includes a controller 42 (shown in FIG. 5) that receives, processes, and transmits the cervical dilation data received from the sensor 38. Preferably, the individual parts of the controller 42 are mounted to a circuit board that is supported within the inner portion 52 (See FIGS. 3A-3D); however, it should be understood that the controller 42 need not be located in the inner portion 52. The controller 42 could be mounted in a separate housing attached to an outer surface of the outer portion 48. For example, the controller 42 includes: a sensor circuit 84 which includes the sensor 38 and a sensor interface located within the controller 42 that generates analog signals related to cervical dilation; an analog-to-digital convertor 88 that converts the analog signals generated by the sensor circuit 84 into digital signals; a processor 92 that receives the digital signals from the analog-to-digital convertor 88, preferably associates the digital signals with a level of cervical dilation, optionally stores the processed (calibration) data into a memory 96, and then transmits this processed data to at least one transceiver 100 that receives the processed data transmitted from the processor 92 and wirelessly transmits the processed data to the wireless unit 18 (shown in FIGS. 6A and 6B).

The cervical monitoring device 14 also includes a power source 44 that provides power to the controller 42. The power source 44 is preferably located within the inner portion 52 of the housing 34, although the power source 44 need not be in this orientation. In a preferred embodiment, the power source 44 is a battery, although the power source 44 may alternatively or in addition include circuits or devices for converting body heat or movement into electrical energy. Preferably, the power source 44, such as a battery, is activated by pressing or rotating the cervical monitoring device 14, for example in response to cervical dilation or contraction. The life duration of the power source 44 will be sufficient to allow operation of the cervical monitoring device 14 throughout the monitoring process. The cervical monitoring device 14 is preferably a single use device that does not require power source 44 replacement.

Figure 4:
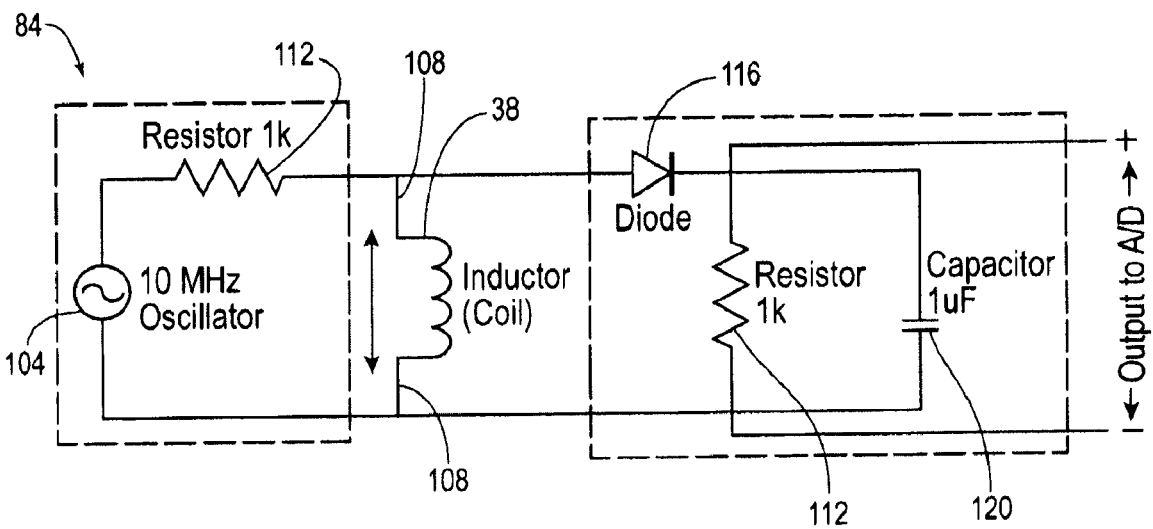
FIG. 4 is a schematic diagram of an exemplary sensor circuit associated with the cervical dilation monitor and constructed in accordance with the present invention.

Referring now to FIG. 4, shown therein is a detailed schematic of a preferred embodiment of the sensor circuit 84. The sensor circuit 84 includes: a sensor interface for supplying electrical current to the sensor 38, as well as a rectifier circuit for generating an analog signal that varies in accordance with changes in dilation detected by the sensor 38. More particularly, the sensor circuit 84 is provided with: an oscillator 104 that generates alternating currents of electrical energy; at least two leads 108 connecting the sensor 38 to the sensor circuit 84 and allowing electrical current generated by the oscillator 104 to pass to and from the sensor 38; at least two resistors 112 that facilitate control of the currents generated by the oscillator 104; at least one diode 116 that converts the alternating electrical currents generated by the oscillator 104 into direct currents; and at least one capacitor 120 responsible for storing electrical energy. As the sensor 38 is stretched apart as a result of an increase in cervical dilation, the inductance properties of the sensor 38 are altered. When the sensor 38 is a coil, the inductance L of the coil in terms of its geometric parameters is given by an empirical formula:

$$L = \frac{0.001 r^2 N^2}{228r + 254S} \quad \text{(Equation 1)}$$

where L is in μH, r is the outer radius of the coil in meters and the length (in meters) of the coil S>0.8 r and N is the number of turns in the coil. The value of inductance predicted by Equation 1 matches well with values calculated by rigorous finite element modeling of the flux linkages of the coil. The formula above is valid in low frequencies when the skin effect is not occurring. At a high frequency the value of the inductance will be about 2% smaller than that given by Equation 1. This alteration in inductance is detected by the sensor 38 and this information is sent to the rectifier circuit (which includes the diode 112, a resistor 116, and the capacitor 120) which generates an analog signal that is sent to the analog-to-digital convertor 88 within the controller 42.

Figure 5:
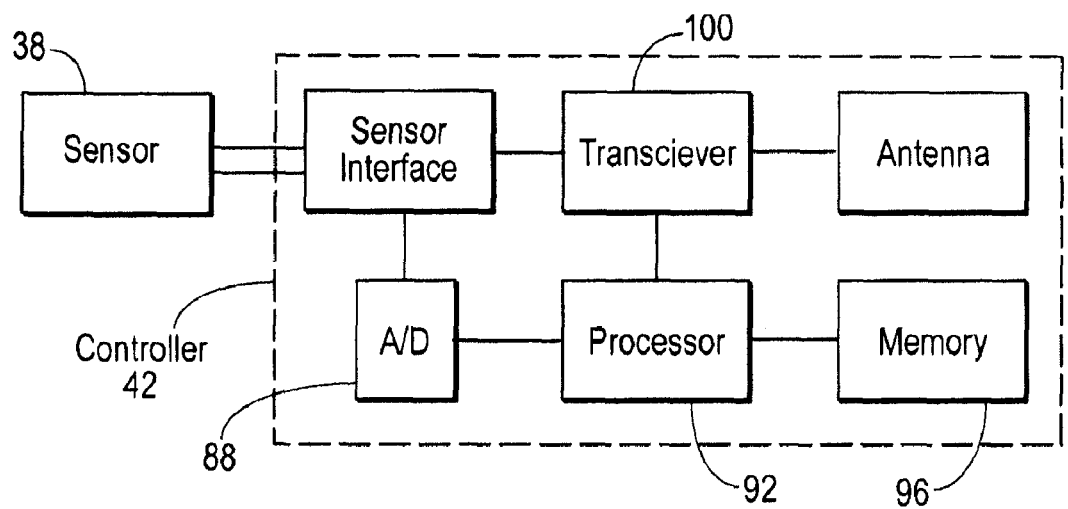
FIG. 5 is a schematic diagram of a controller associated with the cervical dilation monitor and constructed in accordance with the present invention.
Figure 8:
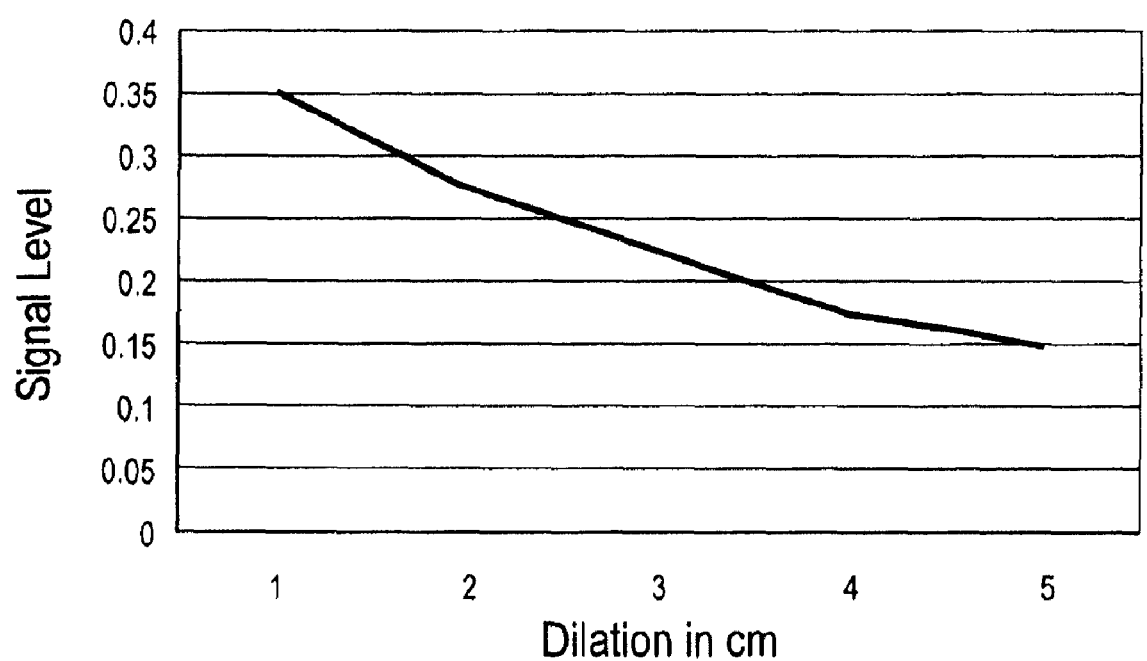
FIG. 8 is a graphical diagram illustrating the correlative relationship between signal level and cervical dilation in centimeters.

Referring now to FIG. 5, shown therein is a block diagram of a preferred embodiment of the controller 42. After the analog signal is generated by the sensor circuit 84, the signal is sent to the analog-to-digital convertor 88, where it is converted into a digital signal indicative of cervical dilation. The digital signal is then sent to the processor 92 which optionally correlates the digital signal to a measurement value (e.g., number of centimeters) of cervical dilation (shown in FIG. 8). This correlation information can be optionally stored in memory 96 for later retrieval or use in converting the digital signal indicative of cervical dulation to the measurement value. The cervical dilation data (i.e., either the digital value or the measurement value) is then sent to the transceiver 100, which wirelessly transmits the cervical dilation data to the wireless unit 18. The transceiver 100 of the controller 42 utilizes a wireless transfer protocol, including, but not limited to, radio frequency (RF), the Zigbee protocol, and/or Sensor Mote technology, all of which are well known in the art, to transmit the correlated data to the wireless unit 18.

Figure 6A:
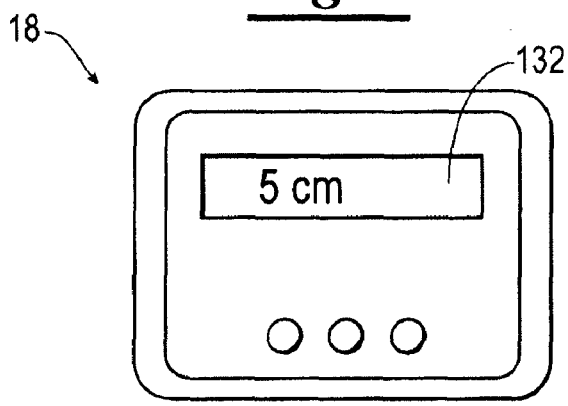
FIG. 6A is a top view of a wireless unit displaying cervical dilation data in centimeters and constructed in accordance with the present invention.
Figure 6B:
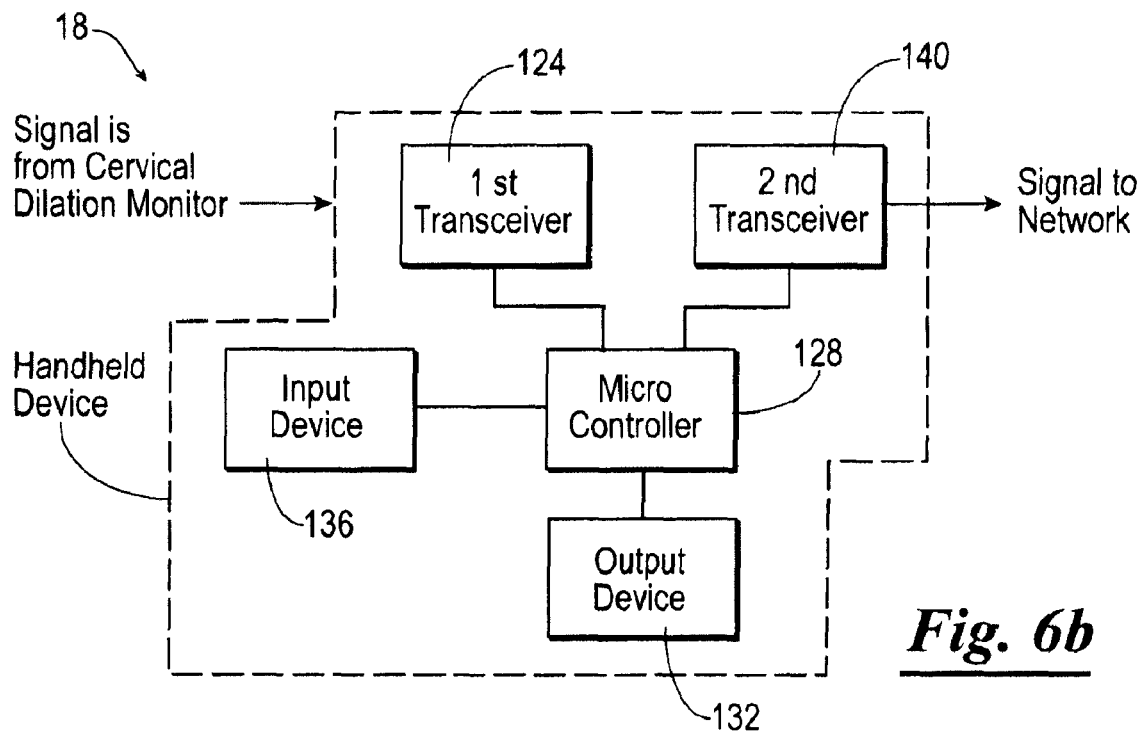
FIG. 6B is a schematic diagram of an exemplary wireless unit constructed in accordance with the present invention.

Referring now to FIGS. 6A and 6B, shown therein is a preferred embodiment of the wireless unit 18. The wireless unit 18, while shown in FIG. 6A as a pager-like device, need not be limited to this construction, and may be any device capable of receiving wireless signals and notifying a user of the measurement data or instructions that will be discussed below by any suitable medium, such as light(s), a display, a pre-recorded message, or the like. For example, the wireless unit 18 can be a computer and computer screen, a cellular phone, or a PDA. In a preferred embodiment, the wireless unit 18 includes: a first transceiver 124 that receives and transmits the correlated data from the controller 42 of the cervical monitoring device 14; a microcontroller 128 that receives the transmitted measurement data or instructions from the first transceiver 124 and sends this information for display on the wireless unit 18; an output device 132 which displays the measurement data sent from microcontroller 128 (and from the transceiver 144 of the remote monitoring system 22) for the user to view; an input device 136 which allows the user to recall previous measurement data displayed on the output device 132 of the wireless unit 18; and a second transceiver 140 which receives the correlation data from the microcontroller 128 and then transmits this data to the remote monitoring system 22 which continuously, and in real-time, monitors the progression of cervical dilation for a pregnant female. The first and second transceivers 124 and 140 of the wireless unit 18 preferably use different types of signals and protocols to communicate. For example, in one embodiment, the wireless unit 18 is adapted to be carried by the pregnant female, and, in this case, the first transceiver 124 is adapted to receive and transmit at short range, e.g., less than 200 feet signals. The wireless unit 18 may however be located many miles from the remote monitoring system 22 and so the second transceiver 140 can be adapted for long range communication. In one example, the first transceiver 124 uses short-range radio frequency and the second transceiver 140 is a cellular phone transceiver.

The wireless unit 18 is designed with the capability of automatically dialing the telephone number of a remote monitoring system 22, such as, but not limited to, a medical data processing agency or call center. Preferably, the dialing is done by the wireless unit 18 at predetermined intervals, for example, every 20 minutes. Once contact with the remote monitoring system 22 is established via the network 20, the wireless unit 18 uploads the cervical dilation data to the remote monitoring system 22.

Figure 9:
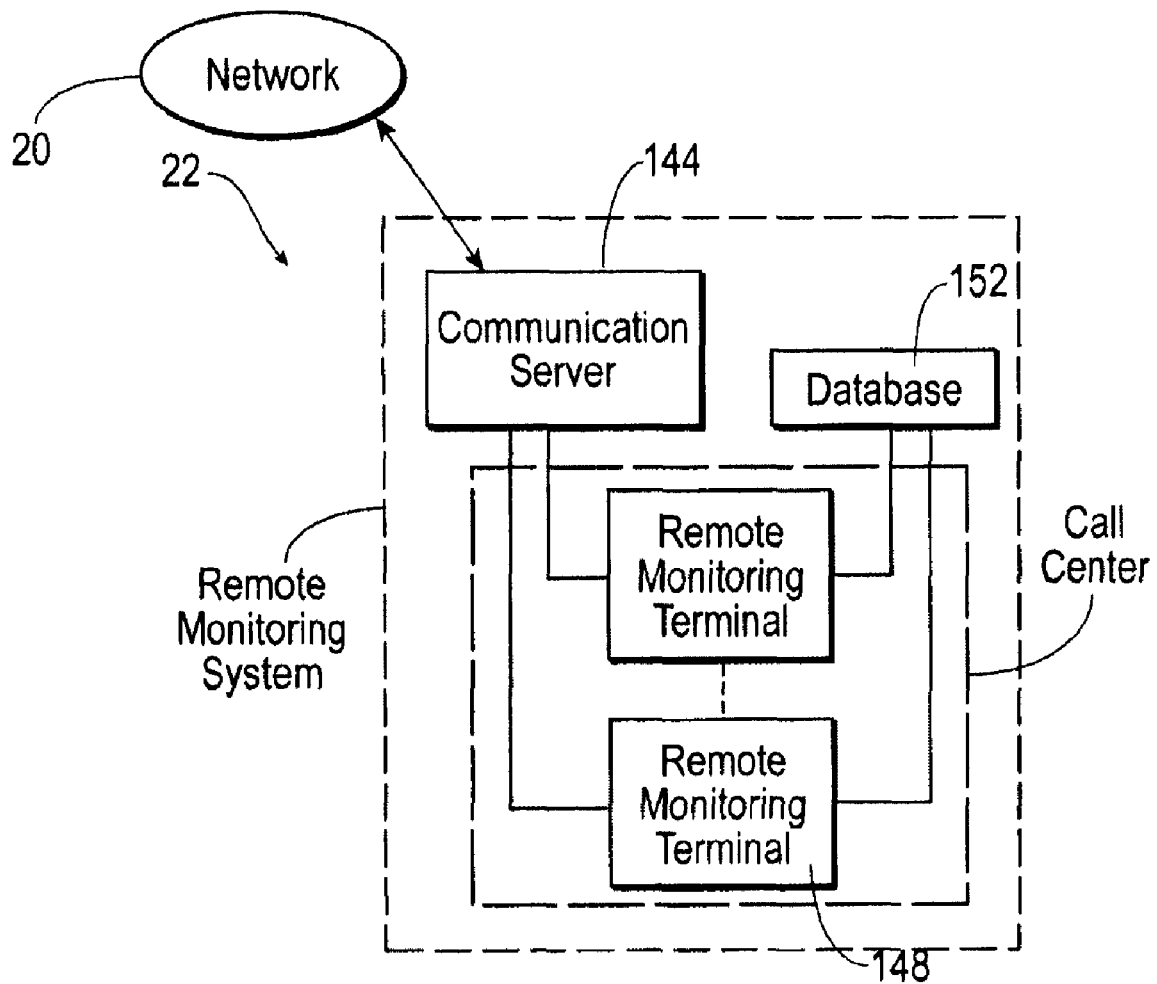
FIG. 9 is a block diagram schematic of a preferred embodiment of a remote monitoring system constructed in accordance with the present invention.

Referring now to FIG. 9, shown therein is a block diagram of a preferred embodiment of the remote monitoring system 22 that continuously and in real-time monitors the cervical dilation of a pregnant woman. In a preferred embodiment, the remote monitoring system 22 includes: a communication server 144 for receiving correlated data from the network 20 and transmitting data regarding the immediacy of labor back to the network 20; at least one remote monitoring terminal 148 for displaying cervical dilation information received from the communication server 144; and a database 152 which is actuated by the communication server 144 to provide patient records and stored correlation data regarding the level of cervical dilation related to the immediacy of labor to the remote monitoring terminal 148.

In general, the remote monitoring system 22 checks the progress of the cervical dilation and provides some basic instructions that are transmitted over the network 20 and displayed to the female on the wireless unit 18. These basic instructions can range from no action needs to be taken to delivery is imminent, prompting the pregnant female to immediately get to the hospital for delivery. If necessary, the remote monitoring system 22 prompts the network 20 to get in touch with the doctor or physician who may then offer medical recommendations to the pregnant female. It should be understood that the connection link between the network 20 and the remote monitoring system 22 can either be a wired or a wireless connection.

Figure 10A:
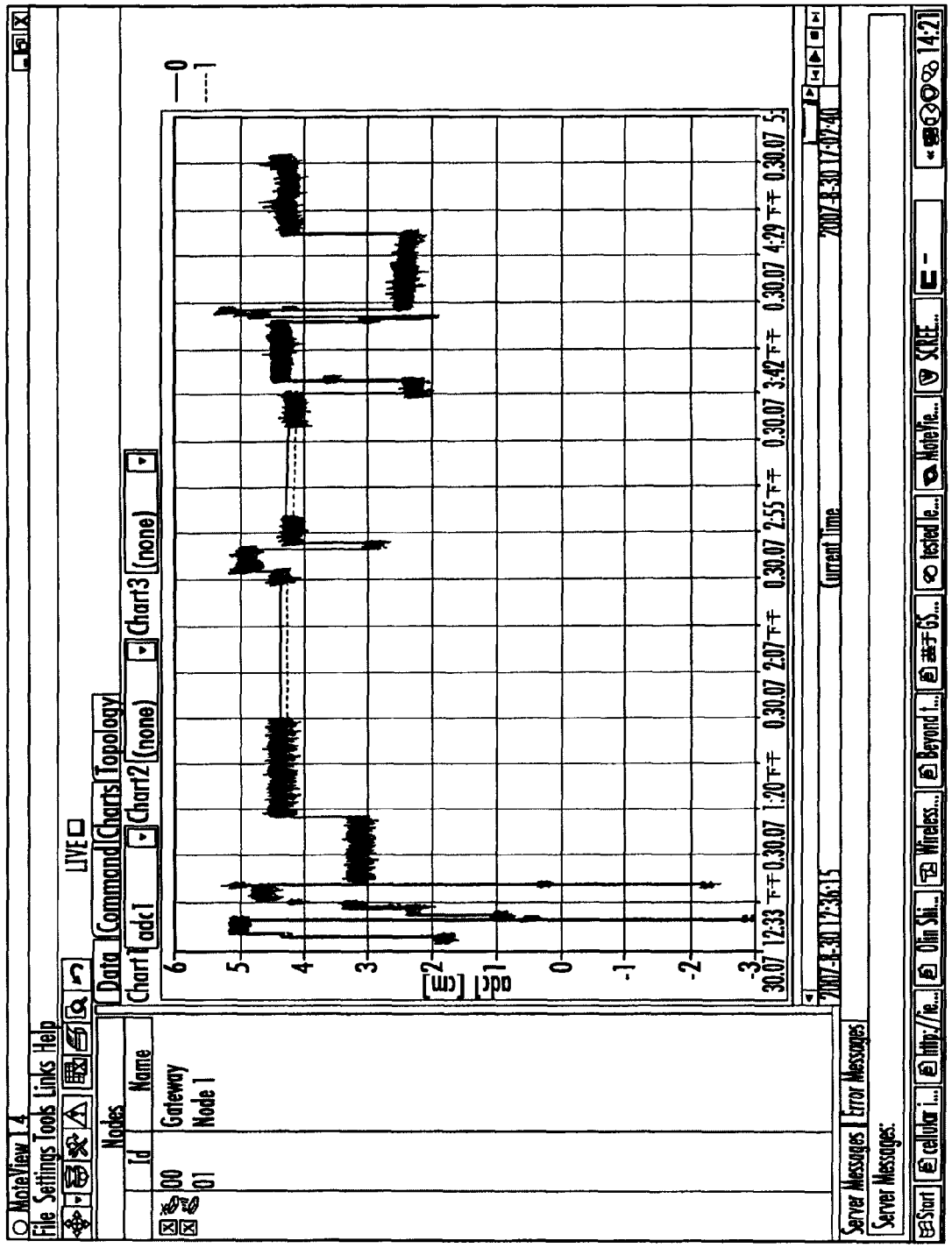
FIG. 10A is a graphical view depicting a signal level displayed on a remote monitoring terminal constructed in accordance with the present invention.

Once the communication server 144 receives the correlated data at predetermined intervals from the network 20, the communication server 144 actuates the database 152 and sends this data to at least one remote monitoring terminal 148, which visually displays the level of cervical dilation over a period of time (as shown in FIGS. 10A and 10B). The remote monitoring terminal 148 accesses the database 152 and compares correlated data with stored information on the database 152 to determine the pregnant female's immediacy of labor. This immediacy data is then re-sent to the communication server 144 which transmits the immediacy data back to the network 20. The network then transmits this data to the wireless unit 18 and, optionally, to the pregnant female's doctor and/or physician. By looking at the immediacy information received from the remote monitoring system 22 via the network 20 and displayed on the output device 132 of the wireless unit 18, the pregnant female can ascertain with reasonable certainty whether she is close to delivery.

In order for the cervical monitoring device 14 to function in accordance with the present invention, it is installed inside the vaginal cavity of the pregnant female. First, the cervical monitoring device 14 is preferably placed within the vaginal cavity by a health care professional, such as a physician or a veterinarian, such that the cervical monitoring device 14 extends across the cervical opening 30. Next, the cervical dilation monitor 14 is attached to portions of the cervical lip 26, typically adjacent to the cervical opening 30. As discussed above, the housing 34 of the cervical dilation monitor 14 can be attached via staples, spikes, stitches or any other biocompatible attachment methodology. In a preferred embodiment, each end of the housing 34 of the cervical dilation monitor 14 is connected to at least two portions of the cervical lip 26, such that the connected cervical dilation monitor 14 slidably extends in response to the level of cervical dilation. For instance, the cervical dilation monitor 14 expands or contracts in response to an increase or decrease in the cervical dilation of the pregnant female. As previously stated, the power source 44 of the cervical dilation monitor 14 is actuated in response to the cervical dilation and contraction.

In a preferred embodiment, the remote cervical dilation monitoring system 10 monitors the cervical dilation utilizing the following methodology. First, the cervical dilation monitor 14 is installed in the pregnant female, as discussed above and actuated to sense the dilation of the cervix in real-time. The cervical dilation monitor 14 then detects a change in the diameter of the pregnant female's cervical opening 30, which is translated into the digital signal indicative of the cervical dilation. Next, the digital signal (or a measurement signal based upon the digital signal) is wirelessly transmitted to the external wireless unit 18 which further transmits the cervical dilation data signal to the remote monitoring system 22. The remote monitoring system 22, by accessing the database 152, correlates the cervical dilation data signal to one or more instructions indicative of the immediacy of delivery. This immediacy data (and/or the instructions) is then transmitted to the network 20 which communicates the immediacy data and/or instructions to the wireless unit 18. Then the user, e.g., the pregnant female or a person caring for the pregnant female, can view the wireless unit 18 to ascertain the immediacy of delivery. Optionally, the network 20 can also transmit the immediacy data to the pregnant female's health care professional(s) so as to notify them of the immediacy of delivery.

Although only one of the cervical dilation monitor 14 and the wireless unit 18 are shown in FIG. 1 for purposes of brevity, it should be understood that the system 10 contemplates the use of multiple cervical dilation monitors 14 and wireless units 18. In one embodiment, the network 20 is adapted to communicate with a large number of wireless units 18 to thereby simultaneously monitor the cervical dilation of a large number of pregnant females in real-time.

Changes may be made in the embodiments of the invention described herein, or in the parts or the elements of the embodiments described herein or in the step or sequence of steps of the methods described herein, without departing from the spirit and/or the scope of the invention as defined in the following claims.

What is claimed is:

1. A cervical dilation monitor for measuring the dilation of a cervix and for providing cervical data to an external wireless unit, the cervical dilation monitor, comprising:
    a housing constructed of bio-compatible material and adapted to be connected to at least two portions of a cervical lip, the housing adapted to expand responsive to cervical dilation;
    a sensor including a coil having an inductance, the coil attached to the housing such that expansion of the housing changes the inductance of the coil to generate signals related to cervical dilation;
    a controller comprising:
        a transceiver that receives and wirelessly transmits the cervical dilation data to the external wireless unit;
        a processor receiving the signals generated by the sensor related to the cervical dilation and enabling the transceiver to wirelessly transmit the cervical dilation data; and
    a power source providing power to the controller.

2. The cervical dilation monitor of claim 1, wherein the power source is internal to the housing.

3. The cervical dilation monitor of claim 1, wherein the power source is external to the housing.

4. The cervical dilation monitor of claim 1, wherein the power source is a battery.

5. The cervical dilation monitor of claim 1, wherein the bio-compatible material is a non-reactive plastic.

6. The cervical dilation monitor of claim 1, wherein the bio-compatible material is stainless steel.

7. The cervical dilation monitor of claim 1, wherein the controller further includes a memory unit for storing the cervical dilation data.

\* \* \* \* \*